United States Patent [19]

Jokinen et al.

[11] Patent Number: 5,068,009

[45] Date of Patent: Nov. 26, 1991

[54] METHOD OF PRODUCING FLUFF PULP WITH IMPROVED DEFIBRATION PROPERTIES

[75] Inventors: Olli Jokinen, Kantvik; Jukka Kettunen; Jarkko Lepo, both of Rauma; Tapio Niemi, Monnanummi; Jaakko E. Laine, Kanvtik, all of Finland

[73] Assignee: Cultor Ltd., Finland

[21] Appl. No.: 497,406

[22] Filed: Mar. 22, 1990

[30] Foreign Application Priority Data

Mar. 30, 1989 [FI] Finland ................................ 891530

[51] Int. Cl.$^5$ .......................... D21C 3/20; D21B 1/02
[52] U.S. Cl. ......................................... 162/9; 162/72; 162/1; 264/517
[58] Field of Search ............................. 162/72, 100, 9; 435/278; 264/517

[56] References Cited

U.S. PATENT DOCUMENTS

| 3,041,246 | 6/1962 | Bolaski et al. | 100/72 B |
| 4,081,316 | 3/1978 | Aberg et al. | 162/100 |
| 4,690,895 | 9/1987 | Farrel | 435/278 |
| 4,923,565 | 5/1990 | Fuentes et al. | 435/278 |

OTHER PUBLICATIONS

Pommier et al., Using Enzymes to Improve the Process and the Product Quality in the Recycled Paper Industry, TAPPI Journal, Jun. 1989, pp. 187–191.

Primary Examiner—Richard V. Fisher
Assistant Examiner—Charles K. Friedman
Attorney, Agent, or Firm—Kenyon & Kenyon

[57] ABSTRACT

Fluff pulp with improved defibration properties is produced by exposing the pulp to an enzyme treatment at any stage during the pulp production process. The enzyme treatment may be carried out using an enzyme preparation containing cellulolytic and/or hemicellulolytic activity. The enzyme treated fluff pulp is useful in the manufacture of disposable hygiene products and air-laid products.

13 Claims, No Drawings

METHOD OF PRODUCING FLUFF PULP WITH IMPROVED DEFIBRATION PROPERTIES

BACKGROUND OF THE INVENTION

The invention relates to a method of producing improved fluff pulps. The invention is also concerned with the use of the improved fluff pulp in disposable hygiene products and air-laid products.

In the invention, the defibration properties of fluff pulp are improved by enzyme treatment.

The worldwide production of fluff pulps amounts to about 2.5 million tons. Softwood with long fibres only is used in the production. More than 90% of the pulps are fully bleached chemical pulps, of which more than 90% are sulphate pulps. The proportion of CTMP (chemithermomechanical pulps) is less than 10%. They are usually peroxide bleached to a degree of brightness of 70 to 80% ISO. TMP (thermomechanical pulp) and groundwood have also been used as fluff pulp though not to any greater degree.

The cooking and bleaching of chemical fluff pulps do not significantly differ from the production of paper pulps. As far as CTM pulpS are concerned, their freeness (drainability) is markedly higher than that of paper pulps, ranging from 500 to 700 ml CSF.

The web formation, wet pressing, and drying of fluff pulps differ greatly from the production of paper pulp. Moreover, these process steps are more critical for the quality and processability of the final product. More than 95% of fluff pulps are delivered to the customer in rolls in which the moisture of the pulp varies between 5 and 10%.

Fluff pulps are used as raw material in the absorbent layers of disposable hygiene products, such as baby diapers, sanitary napkins, panty shields, incontinence pads, and absorbent hospital sheets, as such or with superabsorbents and/or synthetical fibres. More than 80% of the pulps are used in baby diapers.

The most demanding application of fluff pulps is in the so called air-laid products, such as air-laid papers used, e.g., in serving utensils, various towel applications in homes, in the industry and in hospitals. Internationally, the demand of pulp for these products amounts to 70,000 80,000 t/a, and the yearly growth is more than 10%. (Chemical pulp only is used.) Some of the products are colored, whereby either the chemical pulp is colored or the coloring is carried out in connection with the air-laying step.

The dry defibration of pulp (mostly chemical pulp or CTMP) is one of the most important process steps in the production of both napkins and air-laid products. A chemical pulp web (1 to 3 superimposed webs) is thereby led from a roll into a shredder, usually a hammer mill but pin mills and disc refiners can be used as well. In some cases, it is possible to carry out the shredding in two stages, e.g., with a disc refiner and a hammer mill. When using bale pulps, the pulp is first cut into strips which are introduced into the shredder through a separate dosing device. In the shredder, the pulp web is passed between rotating shredding means, such as hammers, and counter blades, positioned at a distance of a few millimeters from each other. This treatment aims at detaching wood fibres contained in the pulp (moisture typically 7%) from each other as undamaged as possible. The shredding process can be assessed by measuring, e.g., decrease in the fibre length, fines or dust formation, and the knot content, i.e., the amount of knots remaining in the pulp (fibre bundles, knots, etc.), and the defibration or shredding energy. The amount of energy required for the production of hygiene products varies within very wide limits, ranging from 80 to 250 MJ per one ton of pulp. The knot content varies in different hygiene products typically from 5 to 30% measured by the SCAN knot tester (SCAN-CM 37:85). Instead, in air-laid products, the knot content should be under 1 %, i.e., the product may contain very little if any knots. The object is to keep the knot level as low as possible with the lowest possible energy consumption while maintaining the fibres undamaged. Excessive consumption of energy does not only result in economical losses but also in other drawbacks such as decreasing fibre lengths, dust formation, and static charging of fibres, which in turn hampers the formation of an even web.

The ratio between the knot content and the energy needed depends mainly on the pulp production process and the density of the pulp web or sheet. Typically, sulphate pulps are "harder", that is, they require more energy than sulphite or CTM pulps. Also, an increase in the density of pulp web caused by wet pressing always increases the energy demand.

With chemical and CTM pulps, attempts have been made to improve the shredding properties of fluff pulp (shredding energy/knot content) by treating the pulp prior to the drying step with debonding chemicals. These, however, always degrade the absorbency of the pulp, and most hygiene product manufacturers do not accept the application of debonding chemicals, wherefore the pulp manufacturers can rely on the debonding treatments only very limitedly.

The most effective way of improving shredding properties is to reduce the density of the pulp web, that is, to prevent the formation of hydrogen bonds between fibres. This, however, always results in a decrease in the drying capacity, which means reduced profitability, because in most fluff pulp factories, it is the drying step that limits the production capacity.

CA patent specification 1,206,305 discloses one solution for improving the shredding properties of fluff pulp. Chemical pulp in the form of an aqueous slurry is therein treated with gaseous ammonia under pressure, whereby the obtained fluff pulp has improved shredding properties. The final product is also recited to exhibit improved absorbency.

However, methods known from the prior art do not offer a satisfactory solution to problems associated with the shredding of fluff pulp.

Examples of enzyme treatment in the production of pulp can be found in the prior art. FR patent specification No. 2,557,894 describes a method of treating chemical pulp with xylanase enzyme with the purpose of shortening the refining time. CA patent specification No. 758,488 is concerned with a method of improving the refining properties of pulp by a cellulase/pectinase/lipase enzyme treatment. FR patent specification No. 2,571,738, in turn, discloses a method in which pulp is provided with special properties by cellulase treatment JP patent specification No. 60,126,395 discloses a method of improving the refining process by enzyme addition.

JP patent specification No. 59,009,299 describes a method in which alkaline cellulase in combination with a surfactant is added to a deinking process for improved deinking.

JP patent application No. 63,059,494 discloses a method of improving the brightness of reclaimed paper pulp by means of alkaline cellulase.

FR patent application No. 8,613,208 describes a method of improving the properties of recycled pulp, e.g., by a cellulase/hemicellulase treatment.

The prior art does not, however, contain any indication of the use of enzyme treatment in the production of fluff pulp.

SUMMARY OF THE INVENTION

The object of the present invention is to improve the shredding properties of fluff pulp by enzyme treatment. It has been found that the enzyme treatment does not affect adversely the other important properties of fluff pulp, such as the fibre length and absorbency. In practice, improved shredding properties reduce the energy demand during the shredding process and decrease the knot content.

In practice, the enzyme treatment of the invention provides the following advantages:

1) the drying capacity of fluff pulps can be substantially increased because the wet pressing of pulp can be increased without deteriorating the shredding properties and because the dry matter content of the pulp prior to drying increases due to the increased wet pressing, and/or 2) the shredding properties can be substantially improved while maintaining the wet pressing and density level and without deteriorating the absorbency.

DETAILED DESCRIPTION OF THE INVENTION

In the invention the enzyme treatment can be carried out at any stage during the fluff pulp production process. The pulp can be treated with enzyme either prior to bleaching, in connection with any pulp bleaching step, or after bleaching. The enzyme treatment can also be carried out in connection with the drying of pulp either before the drying machine or at the drying machine.

In all cases, the enzyme modifies the surface properties of fibres and possible fines so that bonding is reduced and the shredding properties of the pulp are improved.

The enzyme used is preferably cellulase, hemicellulase, or their mixture. Suitable enzyme preparations include Multifect L250 and Multifect K, commercial products manufactured by Finnsugar Ltd. The temperature of the enzyme treatment may range from 10° to 90° C., preferably from 40° to 70° C. The time of treatment depends of the level of enzyme application and the treatment conditions, varying from 10 minutes to one day, preferably from half an hour to 8 hours. The enzyme treatment can be carried out either on stock having a consistency of 0.2 to 20%, preferably of 2 to 12%, or on sheeted web having a dry matter content varying from 1 to 99%, preferably from 20 to 50% or from 80 to 95%.

Suitable dose levels of the different enzymes used according to the invention determined as enzyme activities vary within the following limits (U=activity unit):

| Cellulases: | |
|---|---|
| filter paper activity | 0–20,000 U/kg pulp |
| CMCase activity | 0–500,000 U/kg pulp |
| Hemicellulases: e.g. | |
| xylanase | 0–2,000,000 U/kg pulp |
| mannanase | 0–500,000 U/kg pulp |

The determination of the filter paper activity is described in Ghose, T. K., Patnak, A. N., Bisaria, V. S., Symposium of Enzymatic Hydrolysis of Cellulose, Bailey, M., Enari T. M., Linko, M., Eds. (SITRA, Aulanko, Finland, 1975), 111–136. CMCase (carboxymethyl cellulase) activity determination is described in Mandels, M., Weber, J., Adv. Chem. Ser 95 (1969) 391–413; and xylanase activity determination in Khan, A. W., Tremblay, D., LeDuy, A., Enzyme Microb. Technol., 8 (1986) 373–377.

The mannanase activity was determined as follows: 1 ml of enzyme was added to 1 ml of Locust bean gum solution (0.5%, Sigma No. G-0753, prepared in 50-mM sodium citrate buffer, pH 5.3), suitably diluted in the same buffer. The solution was incubated at 50° C. in a water bath for 10 minutes. The reaction was stopped by adding 3 ml of DNS reagent and the colour was developed by cooking for 5 minutes. Absorbance was measured at a wave length of 540 nm. One enzyme unit (U) releases one micromole of reducing sugars calculated as mannose per minute under assay conditions.

In the following the invention will be described more closely by means of working examples.

EXAMPLE 1

A laboratory experiment was carried out on a fluff pulp manufactured from a mixture of spruce and pine chips by the NS-AQ (neutral sulphite-anthraquinone) method and bleached by a O—D—E═—D sequence (oxygen -chlorine dioxide -alkali extraction strengthened with oxygen -chlorine dioxide). The pulp had been taken from the factory out of a washing filter after the bleaching step for the laboratory-scale enzyme treatment experiments. The enzyme treatment was carried out under the following conditions:

| temperature | 50° C. |
|---|---|
| pH | 5.0 |
| time | 2 hours |
| consistency | 3% |

The enzyme preparations used and their activities appear from Table 1.

TABLE 1

| Enzyme preparations used and their activities | | |
|---|---|---|
| | Enzyme | |
| | Multifect L250 | Multifect K |
| CMCase activ. U/ml | 2,800 | 800 |
| Xylanase activ. U/ml | 500 | 5,000 |
| Filter paper activ. U/ml | 110 | 40 |
| Mannanase activ. U/ml | 90 | 190 |

Enzyme dosages were 0 (. control), and 2 and 5 liters per 1,000 kg pulp on dry basis (1/ton). The enzyme amounts added appear from the following Table 2 (given as enzyme units per kg of pulp on dry basis).

TABLE 2

| Enzyme | Dosage (1/ton) | Added enzyme amounts per kg of pulp on dry basis | | | |
|---|---|---|---|---|---|
| | | CMCase act. U/kg | Xylanase act. U/kg | Filter paper act. U/kg | Mannanase act. U/kg |
| Multifect L250 | 2 | 5,600 | 1,000 | 220 | 180 |
| Multifect L250 | 5 | 14,000 | 2,500 | 550 | 450 |
| Multifect K | 2 | 1,600 | 10,000 | 80 | 380 |
| Multifect K | 5 | 4,000 | 25,000 | 200 | 950 |

After the enzyme treatment/control treatment, so called fluff sheets were prepared from the pulp, aiming at a grammage of 600 g/m:. The sheets were prepared with a so called hand large sheet mould (. hand sheet mould model KCL but larger in size, KCL.Finnish Pulp and Paper Research Institute). After preparation the sheets were pressed (10 bar, 3 min) and dried (air drying: 80° C., 8 h).

After drying the sheets were aerated and tested, that is, dry shredded, and the properties of fluff pulp were measured. The test results appear from the following Table 3.

TABLE 3

| Enzyme | Dosage 1/ton | Shredding properties of the sheets | | | |
|---|---|---|---|---|---|
| | | Energy required for shredding MJ/ton | Knot content after shredding % | Fibre length of fluff pulp after shredding mm | Absorpt. time (SCAN) of fluff pulp after shredding s |
| Control 1 | — | 172 | 17 | 2.12 | 3.6 |
| Control 2 | — | 168 | 19 | 2.05 | 3.2 |
| Control 3 | — | 170 | 14 | 2.03 | 4.0 |
| Multifect L250 | 2 | 134 | 8 | 2.00 | 3.6 |
| Multifect L250 | 5 | 123 | 19 | 1.87 | 5.3 |
| Multifect K | 2 | 145 | 8 | 2.01 | 3.6 |
| Multifect K | 5 | 130 | 12 | 1.98 | 3.1 |

The control treatments were carried out three times in order to see the distribution of the test results. It appears very clearly from Table 3 that the enzyme treatment improves the shredding properties of pulp (reduced energy requirement and knot content). The enzyme treatments did not affect the other important properties of fluff pulp (fibre length and absorption time).

EXAMPLE 2

The experiment of Example 1 was repeated in such a manner that the temperature of enzyme treatment was 45° C. and the density of the prepared fluff sheets was adjusted to a constant value 540 kg/ms while the grammage was 760 g/m:. Otherwise the experiment arrangement and conditions were the same as in Example 1. The enzyme amounts added appear from Table 4 and the test results from Table 5.

TABLE 4

| | Enzyme amounts added per kg of pulp on dry basis | |
|---|---|---|
| | Enzyme | |
| | Multifect L250 | Multifect L250 |
| Dosage (1/ton) | 1.0 | 2.0 |
| CMC activ. U/kg | 2,800 | 5,600 |
| Xylanase activ. U/kg | 500 | 1,000 |
| Filter paper activ. U/kg | 110 | 220 |
| Mannanase activ. U/kg | 90 | 180 |

TABLE 5

| Enzyme | Dosage 1/ton | Shredding properties of the sheets | |
|---|---|---|---|
| | | Energy required for shredding MJ/t | Knot content after shredding % |
| — | — | 173 | 17 |
| Multifect L250 | 1.0 | 160 | 14 |
| Multifect L250 | 2.0 | 157 | 13 |

It appears from Table 4 that the enzyme treatment has improved the shredding properties of the pulp in this case, too.

EXAMPLE 3

A mill scale enzyme treatment experiment was carried out with the NS-AQ pulp mentioned in Example 1. Diluted enzyme solution was introduced at the pump, pumping the pulp from the storage tower to the machine chest of the drying machine. The conditions during the enzyme treatment were as follows:
temperature 43°–45° C.—ph 4.5–5.0
pulp consistency about 3%
reaction time 1.5 hours.

The average enzyme dosage during the trial was 1.1 liters calculated on 1,000 kg of dry pulp (1/t) and thus the enzyme dosages calculated as enzyme activities (U/kg) on kg of dry pulp were as given in the following Table 6.

TABLE 6

| Enzyme dosage expressed as enzyme activities on of dry pulp. | |
|---|---|
| Dosage, 1/t | 1.1 |
| CMCase activity, U/kg | 3,080 |
| Xylanase activity, U/kg | 550 |
| Filter paper activity, U/kg | 121 |
| Mannanase activity, U/kg | 99 |

The enzyme trial lasted for 45 hours. The density of the pulp was kept constant (0.56 kg/dm3). During the trial the performance of the drying machine was monitored and the final pulp was tested according to the methods mentioned in Example 1. In addition, the drying machine performance was monitored and control samples of the pulp were tested 4 hours before the addition of enzyme was started and 3 hours after the addition of enzyme was stopped. A summary of the results is shown in Table 7.

The results in Table 7 show clearly that the treatment of the pulp with cellulolytic and hemi-cellulolytic enzymes has improved the fluffability, i.e., the shredding properties of NS-AQ pulp also in mill scale.

TABLE 7

The effect of enzyme treatment (Multifect L250) on drying machine performance and shredding properties of pulp for NS-AQ fluff pulp. The comparison between the control and the enzyme treated pulp is made at constant density (0.560 kg/dm³).

|  | Control (no enzyme) | 1.1 l/t Multifect L250 |
| --- | --- | --- |
| Drying machine: | | |
| Wet pressing, kN/m | 92 | 85 |
| Machine speed, m/min | <85 | 92 |
| production, t/h | 18 | >20 |
| Burst, kPa | >1,500 | <1,200 |
| Shredding properties: | | |
| Energy consumption, MJ/t | 220 | 200-205 |
| Knots, % | 12 | 7 |
| Bulk, cms/g | 20.5 | 21.0 |
| aged | 21.5 | 22.0 |
| Absorption time, s | 2.7 | 2.8 |
| aged | 3.1 | 3.2 |
| Absorption capacity, g/g | 11.0 | 11.3 |
| aged | 11.1 | 11.6 |

EXAMPLE 4

O—C+D—E—O—D—E—D (oxygen -mixture of chlorine and chlorine dioxide -alkali extraction -oxygen -chlorine dioxide -alkali extraction -chlorine dioxide bleached softwood (pine/spruce) sulphate pulp was taken from the mill from the dilution tank before the drying machine to the laboratory for enzyme treatment experiments. The enzymatic treatments were carried out using the following conditions:
temperature 50 C.—pH 5.0
reaction time 1 hour
pulp consistency 3%

The enzyme preparations used and their corresponding activities appear from Table 8.

TABLE 8

Enzyme preparations and their activities

|  | Multifect L250 | Multifect L250/ Multifect K |
| --- | --- | --- |
| CMCase activity, U/ml | 2,800 | 1,800 |
| Xylanase activity, U/ml | 500 | 2,750 |
| Filter paper activity, U/ml | 110 | 75 |
| Mannanase activity, U/ml | 90 | 140 |

Enzyme dosages of 0 (. control) and 1, 2, and 4 liters on 1,000 kg of dry pulp were used. The corresponding enzyme activities calculated on kg of dry pulp appear from Table 9.

After the enzyme treatment and the control treatment, fluff sheets were prepared from the pulp in the same way as in Example 1 and the sheets were tested according to the methods in Example 1. The results are shown in Table 10.

It is evident from the results in Table 10 that the shredding properties of sulphate pulp are also improved by the enzyme treatment. That means lower shredding energy consumption and lower knot content for the enzymatically treated pulp compared with the control.

TABLE 9

Added enzyme amounts calculated as enzyme activities on kg of dry pulp

| Enzyme | Dosage l/t | CMCase U/kg | Xylanase U/kg | FPU U/kg | Mannanase U/kg |
| --- | --- | --- | --- | --- | --- |
| Multifect L250 | 1 | 2,800 | 500 | 110 | 90 |
| Multifect L250 | 2 | 5,600 | 1,000 | 220 | 180 |
| Multifect L250 | 4 | 11,200 | 2,000 | 440 | 360 |
| Multifect L250/Multifect K | 1 | 1,800 | 2,750 | 75 | 140 |
| Multifect L250/Multifect K | 2 | 3,600 | 5,500 | 150 | 280 |
| Multifect L250/Multifect K | 4 | 7,200 | 11,000 | 300 | 560 |

TABLE 10

Fluffing (shredding) properties of enzyme treated sulphate pulp sheets.

| Enzyme | Dosage l/t | Fluffing Energy consumption, MJ/t | Knots % | Absorpt. time, s |
| --- | --- | --- | --- | --- |
| Control | — | 139 | 12 | 4.2 |
| Multifect L250 | 1 | 130 | 10 | 3.9 |
| Multifect L250 | 2 | 121 | 12 | 4.4 |
| Multifect L250 | 4 | 117 | 9 | 4.9 |
| Multifect L250/Multifect K | 1 | 126 | 10 | 3.9 |
| Multifect L250/Multifect K | 2 | 124 | 9 | 4.0 |
| Multifect L250/Multifect K | 4 | 116 | 9 | 4.8 |

EXAMPLE 5

A similar test as in Example 1 was carried out with O—D—E=p—D (oxygen -chlorine dioxide -alkali extraction strengthened with oxygen+peroxide -chlorine dioxide) bleached spruce bisulphite-soda pulp. Bleached pulp was taken from the last drum washer before the pulp storage tank. The experimental conditions were the same as in Example 1 with the exception that a reaction time of 1 hour was used instead of 2 hours. The amounts of added enzyme and the corresponding activities are shown in Table 11 and the sheet test data in Table 12.

TABLE 11

Added amounts of Multifect L250 enzyme calculated as enzyme activities on kg of dry pulp.

|  | Dosage, l/t | | |
| --- | --- | --- | --- |
|  | 1 | 2 | 4 |
| CMCase activity, U/kg | 2,800 | 5,600 | 11,200 |
| Xylanase activity, U/kg | 500 | 1,000 | 2,000 |

TABLE 11-continued

| Added amounts of Multifect L250 enzyme calculated as enzyme activities on kg of dry pulp. | | | |
|---|---|---|---|
| | Dosage, l/t | | |
| | 1 | 2 | 4 |
| Filter paper activity, U/kg | 110 | 220 | 440 |
| Mannanase activity, U/kg | g0 | 180 | 360 |

TABLE 12

| Shredding properties of the sheets. | | | |
|---|---|---|---|
| Enzyme | Dosage l/t | Shredding energy consumption, MJ/t | Knots % |
| Control | | 100 | 1 |
| Multifect L250 | 1 | 96 | 0 |
| | 2 | 96 | 0 |
| | 4 | 86 | 0 |

It appears from Table 12 that the enzyme treatment also improves the shredding properties of bisulphite-soda pulp.

The foregoing general discussion and experimental examples are intended to be illustrative of the present invention, and are not to be considered as limiting. Other variations within the spirit and scope of this invention are possible and will present themselves to those skilled in the art.

We claim:

1. A method of producing fluff pulp with improved shredding properties comprising adding an enzyme having cellulolytic and/or hemicellulolytic activity to wood pump at some point prior to shredding to form said fluff pulp, the enzyme being added in an amount sufficient to improve the shredding properties of the pulp.

2. The method according to claim 1, wherein said fluff pulp is selected from the group consisting of chemical pulp, chemi-thermomechanical pulp, thermomechanical pulp and chips.

3. The method according to claim 2, wherein said pulp is unbleached pulp.

4. The method according to claim 2, further comprising a bleaching step.

5. The method according to claim 4, wherein said enzyme treatment is carried out prior to the bleaching step.

6. The method according to claim 4, wherein said enzyme treatment is carried out in connection with any pulp bleaching step.

7. The method according to claim 4, wherein said enzyme treatment is carried out after the bleaching step.

8. The method according to any one of the preceding claims, wherein said enzyme treatment is carried out in connection with the drying of the pulp.

9. The method according to claim 1, wherein said enzyme treatment is carried out by using an enzyme preparation containing cellulolytic activity and/or hemicellylolytic activity.

10. The method according to claim 9, wherein said enzyme preparation is added in an amount equivalent to 0 to 10,000 units of cellulolytic activity determined as filter paper activity; 0–200,000 units of cellulolytic activity determined as CMCase activity; 0–2,000,000 units of hemicelluloylytic activity determined as xylanase activity; and/or 0–500,000 units of hemicellulolytic activity determined as mannanase activity, per kg of pulp on dry basis.

11. The method according to claim 9, wherein said enzyme preparation is added in an amount equivalent to about 20–600 units of cellulolytic activity determined as filter paper activity; about 500–10,000 units of cellulolytic activity determined as CMCase activity; about 500–100,000 units of hemicellulolytic activity determined as xylanase activity; and/or about 50–10,000 units of hemicellulolytic activity determined as mannanase activity, per kg of pulp on dry basis.

12. A method of manufacturing disposable hygiene products comprising using as a component a fluff pulp produced by the method of claim 1.

13. A method of manufacturing air-laid products comprising using as a component a fluff pulp produced by the method of claim 1.

* * * * *